United States Patent [19]
Heske et al.

[11] Patent Number: 5,749,887
[45] Date of Patent: May 12, 1998

[54] TWISTED STRAND LOCALIZATION WIRE

[75] Inventors: Norbert Heske; Thomas Heske, both of Turkenfeld, Germany

[73] Assignee: C. R. Bard, Inc., Murray Hill, N.J.

[21] Appl. No.: 457,480

[22] Filed: Jun. 1, 1995

[30] Foreign Application Priority Data

Jul. 13, 1994 [DE] Germany .............. 44 24 394.4

[51] Int. Cl.⁶ .................................................. A61B 17/34
[52] U.S. Cl. .................. 606/185; 604/116; 604/117; 128/899; 128/754
[58] Field of Search ..................... 606/185, 116, 606/223, 224; 604/164, 117, 264, 165, 116; 128/899, 754

[56] References Cited

U.S. PATENT DOCUMENTS 5,158,084  10/1992  Ghiatas ........................... 604/117

Primary Examiner—Robert A. Hafer
Assistant Examiner—Justine R. Yu
Attorney, Agent, or Firm—Jones & Askew, LLP

[57] ABSTRACT

A device for marking tissue locations is disclosed in which a localization wire comprises multiple strands twisted together. At predetermined spaced intervals along the length of the localization wire, the strands are twisted together more densely than along the remaining portion of the wire, providing readily identifiable markers which can be visualized under ultrasound or X-ray or can be felt by the physician's fingertips. The free forward end of each of the twisted strands is formed into a barb to anchor the forward end of the localization wire within the patient's tissues.

8 Claims, 4 Drawing Sheets

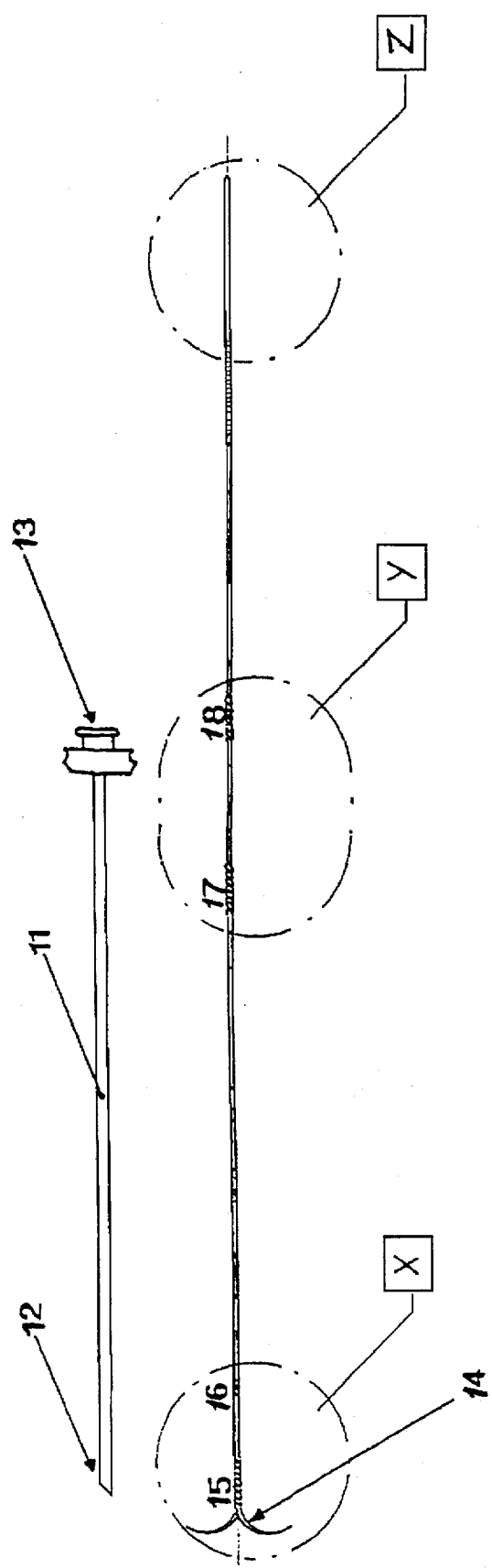

TWISTED STRAND LOCALIZATION WIRE

TECHNICAL FIELD

The present invention pertains to a device for marking tissue locations, comprising barbs at the forward end of the device for anchoring the device at a predetermined location within the tissues. More specifically, the invention relates to a localization wire comprising two wires twisted together along their respective lengths to form a dual-strand wire, the forward end of each strand being twisted into the shape of a barb.

BACKGROUND OF THE INVENTION

Numerous devices for marking tissue locations are known wherein a hollow needle is provided with a cutting point on its distal end and through which a wire-like localization device can be inserted to mark the location of suspect tissue. One example of such a device for marking locations of suspect tissue is disclosed in World Patent No. 90/15576. This device comprises a hollow needle through which a localization wire is inserted. The localization wire has sections that are bent in the shape of a helix such that the localization wire can be inserted by turning in the manner of a corkscrew and remain at the tissue location to be marked in a largely stationary fashion. In addition, the aforementioned publication discloses an extensive summary of known marking devices.

All known tissue marking devices have a hollow needle which is introduced into the body, usually under local anesthesia, at a location that is situated very close to the suspect tissue location. Subsequently, a marking wire is guided through the hollow needle and fixed inside the defective tissue location in such a way that the locating of this particular tissue location is simplified for observation and treatment during subsequent surgical procedures, e.g., tissue removal by means of a biopsy. After the damaged tissue has been marked with the marking wire, the hollow needle is removed from the body such that the marking wire remains at the marked location and protrudes longitudinally from the human body. However, it frequently occurs that the introduced marking wires are displaced from their original position due to movements in the interior of the body.

Even those marking devices known from the state of the art which are designed in the shape of a corkscrew at their distal end in order to make it possible to anchor the marking device in the tissue by torsion or to allow an exact positioning of the marking device by subsequently turning the corkscrew forward or backward are unable to insure an entirely stationary anchoring of the system in the tissue to be examined.

Another disadvantage of these known systems for marking tissue locations is that the cost of manufacturing helical marking wire arrangements is undesirably high.

BRIEF SUMMARY OF THE INVENTION

The invention is based on the objective of developing a device for marking tissue locations, comprising a hollow needle that is provided with a cutting point at its distal end and through which a wire-like localization wire can be inserted at the tissue location to be marked, in such a way that it is insured that the localization wire is anchored in stationary fashion after being inserted at the tissue location, and that the manufacturing costs of such a device can be substantially reduced as compared to conventional devices of this type.

According to the disclosed embodiment of the invention, a device for marking tissue locations comprises a hollow needle that is provided with a cutting point at its distal end and through which a wire-like localization wire can be inserted at the tissue location to be marked. The device is characterized by the fact that the localization wire comprises at least two twisted wire strands, the distal end sections of which are deformable and designed in the shape of a barb.

The twisting of the two wires according to the invention not only provides additional stability along the longitudinal axis of the wire, but also makes it possible to place markings along the longitudinal axis of the wire without requiring additional marking materials by twisting predetermined sections of the wire more tightly such that the twists are more dense than the major portion of the wire.

Only one continuous wire with a diameter of, for example, 0.3 mm is used for manufacturing a marking wire according to the disclosed embodiment of the invention. This wire is bent centrally such that the two identically long wire halves are formed. Subsequently, the two wire halves are mutually twisted except for the two wire ends which usually remain untwisted for a length of approximately 1 to 2 cm. These wire end sections are subsequently bent away from the longitudinal axis of the wire in the shape of an arc, i.e., in opposite directions.

The arc-shaped deformation of the wire ends remains unchanged if the selected wire material has a certain minimum rigidity. Consequently, the insertion of a wire strand so designed into a thin hollow needle does not cause the arc-shaped curvature to straighten. To insure further that the shape of the wire and sections remains unchanged, it is advantageous if the finished localization wire is heat-treated at temperatures of approximately 500° C. (932° F.) such that material hardening takes place.

According to the invention, the pre-bending of the distal end sections of the marking wire into the shape of a barb insures that the localization wire, once inserted, remains at the tissue location to be marked in a stationary fashion, so that the transport of the examined and "marked" patient to the operating room does not cause a displacement of the tip of the marking wire in the body tissue.

Thus, it is an object of the present invention to provide an improved tissue localization wire.

It is a further object of the present invention to provide a tissue localization wire which provides improved anchoring of the forward end of the wire in the tissue to be examined.

Still another object of the present invention is to provide a tissue localization wire which is easy and inexpensive to manufacture.

It is yet another object of the present invention to provide a tissue localization wire having marker locations at spaced intervals along its length which permit the physician to identify such marked locations both tactilely and using visualization apparatus such as ultrasound, X-rays, and the like.

Other objects, features, and advantages of the present invention will become apparent upon reading the following specification, when taken in conjunction with the appended claims.

DESCRIPTION OF THE DRAWINGS

FIG. 1 is a side view of the localization wire and a hollow needle according to the present invention.

DETAILED DESCRIPTION OF THE DISCLOSED EMBODIMENT

Referring now in more detail to the drawings, in which like numerals indicate like elements throughout the several views, FIG. 1 shows a hollow needle 11, the forward end of which is provided with a cutting point 12, and the rearward end of which is provided with a handle 13 for manipulating the hollow needle.

Figures 3A, 3B:
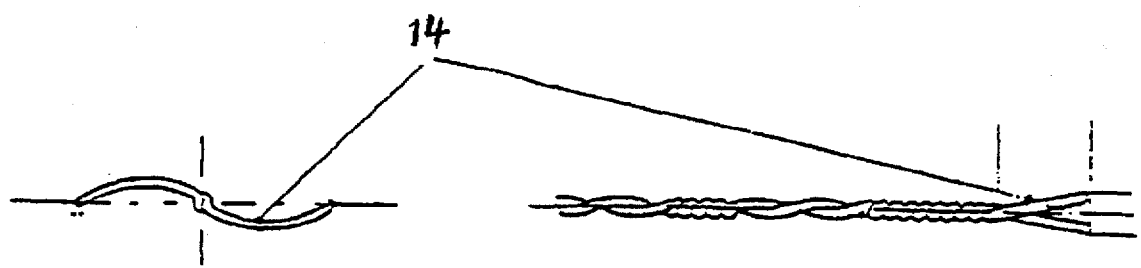
FIG. 3A is an end view of the forward end of the localization wire of FIG. 1 showing the configuration of the barbs which anchor the localization wire in the target tissue.
FIG. 3B is a side view of the forward end of the localization wire.

The localization wire according to the invention which is shown in FIG. 3B can be advantageously inserted through the cutting point 12 of the hollow needle 11. In this case, the localization wire is inserted until the forward end section 14 of the localization wire which is designed in the shape of an arc is entirely retracted within the hollow needle 11.

Along its longitudinal axis, the localization wire includes marker sections 15, 16, 17 and 18 in which the wires are twisted more densely than along the remaining region of the wire. A detailed illustration of the twisted wires within the remaining wire region was omitted so as to provide a clearer illustration. In this case, the arrangement and the length of the respective regions 15, 16, 17 and 18 were chosen such that the following advantages are attained:

Once the localization wire is entirely inserted into the hollow needle 11, the hollow needle can be inserted into the human body so as to mark tissue locations to be examined. The positioning of the hollow needle 11 is carried out with the aid of visualization systems, e.g., X-ray or ultrasound methods. Once the needle is positioned at the correct location, the surgeon pushes the localization wire out of the forward end of the hollow needle 11, so that the forward end section of the localization wire which is designed in the shape of an arc protrudes entirely from the hollow needle. To verify that the end section of the localization wire protrudes entirely from the hollow needle, the rearward end of the twisted section 18, which the surgeon can sense with his fingertips, still needs to protrude from the rearward end of the hollow needle 11. Consequently, the surgeon can easily ascertain if the localization wire protrudes entirely from the hollow needle with its forward end sections 14 within the intracorporeal region. The twisted section 17 fulfills the same function as the previously described twisted section 18 if a shorter hollow needle is used.

In instances in which the surgeon must surgically treat or remove the tissue location to be examined, the surgeon carefully cuts open the body region along the extent of the wire and literally senses with his fingertips that, e.g., once he reaches the twisted sections 15 or 16 he has almost reached the forward end of the localization wire indicating the exact position of the tissue location. Depending on the surgical method used, the forward region of the marking wire can be placed in front, in the center of, or behind the tissue location to be examined, so that the previously described twisted sections 15 and 16 represent auxiliary markings that can be sensed by the surgeon so as to ascertain the exact position of the tissue location relative to the longitudinal axis of the wire.

Figure 2A:
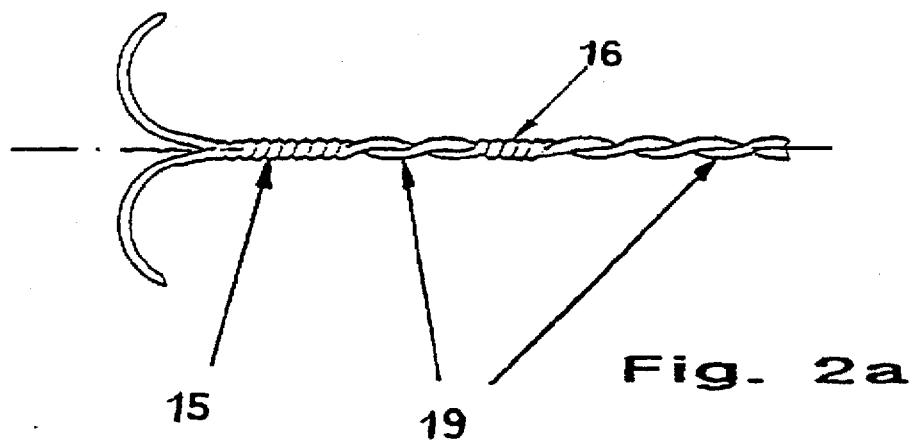
FIGS. 2A and 2B are detailed views of the twisted wires along the localization wire of FIG. 1.
Figure 2B:
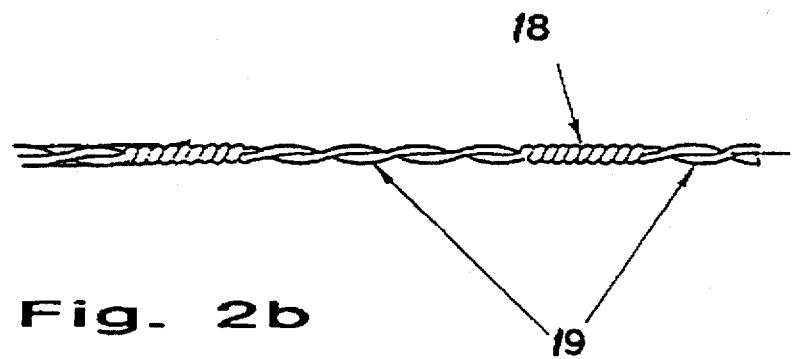
Figure 2C:
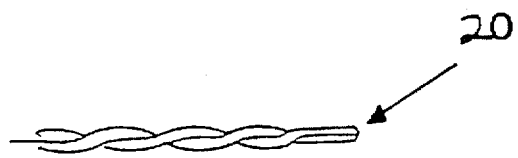
FIG. 2C is a side view of the forward end region of a localization wire of FIG. 1.

The regions X, Y and Z shown in the lower portion of FIG. 1 correspond to the detailed representations shown in FIGS. 2A, 2B and 2C.

FIG. 2A shows the forward region of the localization wire in the form of an enlarged representation. The forward end sections 14 of the wire which are bent outward in the shape of an arc preferably are rounded at their forward ends to eliminate any sharp-edges. The previously described twisted sections 15 and 16 are preferably twisted with a density of five turns per 10 mm and are separated from one another by a twisted section 19 that is twisted less densely. The twisted section 19 preferably is twisted with one turn per 8 mm.

FIG. 2B represents the central region Y in FIG. 1. This region comprises the twisted sections 17 and 18 which, depending on the length of the hollow needle 11, fulfill the function of indicating if the forward end section of the localization wire protrudes entirely from the hollow needle 11.

FIG. 2C shows the rearward end of the localization wire. This figure shows that the two twisted wire sections are formed by bending one wire centrally at its midpoint 10.

It is advantageous if the forward end sections 14 of the localization wire are bent in the shape of a propeller as shown in FIG. 3A. FIG. 3B shows that the end sections of the localization wire which are bent in the shape of an arc are deformed in such a way that they are bent relative to the longitudinal axis of the wire strand in different planes. Stated differently, the barbs are curved both in a plane passing through the longitudinal axis of the localization wire and also in a plane transverse to the longitudinal axis of the localization wire. This measure makes it impossible for the wire tips to move back and forth in their respective planes.

It is also possible to manufacture the localization wire according to invention of two, four or more pairs of twisted wires, so that an anchoring tip with multiple wire end sections can be provided within the forward region of the localization wire.

It will be understood that the foregoing embodiment has been disclosed by way of example, and that other modifications may occur to those skilled in the art without departing from the scope and spirit of the appended claims.

What is claimed is:

1. A device for marking tissue locations, comprising:

a hollow needle having a cutting point at its forward end;

a localization wire dimensioned to be inserted through said hollow needle, said localization wire including at least two twisted wire strands, said at least two twisted wire strands having forward ends, said forward ends of said wire strands being formed into barbs.

2. The device of claim 1, wherein said localization wire comprises a continuous piece of wire, wherein said continuous piece of wire has a midpoint dividing said continuous piece of wire into two halves, wherein said continuous piece of wire is bent at its midpoint, and wherein said halves of said continuous piece of wire are twisted together.

3. The device of claim 1, wherein said localization wire is comprised of sections along which said two wire strands are twisted at a first twist density, separated by sections along which said two wire strands are twisted at a second density which is different from said first density.

4. The device of claim 3, wherein said first twist density comprises approximately five turns of said two wire strands for each 10 mm. of length of said localization wire, and wherein said second twist density comprises approximately one turn of said two wire strands for each 8 mm. of length of said localization wire.

5. The device of claim 3, wherein said hollow needle has a rearward end, and wherein at least one of said sections along which said two wire strands are twisted at said first twist density is located at a position along said localization wire such that said at least one section extends from the rearward end of said hollow needle when said forward ends of said twisted wire strands are completely extended from the forward end of said hollow needle.

6. The device of claim 1, wherein said localization wire comprises a longitudinal axis, and wherein each of said barbs is formed in the shape of an arc extending outward from said longitudinal axis.

7. The device of claim 1, wherein said forward ends of said twisted wire strands have rounded edges.

8. The device of claim 1, wherein said localization wire comprises a shape memory, whereby said barbs can be straightened to retract said localization wire into said hollow needle, said barbs returning to an arcuate configuration upon being extended from said hollow needle.

* * * * *